US011633174B2

(12) United States Patent
Lee et al.

(10) Patent No.: US 11,633,174 B2
(45) Date of Patent: *Apr. 25, 2023

(54) ULTRASOUND SYSTEM AND SIGNAL PROCESSING UNIT CONFIGURED FOR TIME GAIN AND LATERAL GAIN COMPENSATION

(71) Applicant: SAMSUNG MEDISON CO., LTD., Gangwon-do (KR)

(72) Inventors: Doo Sik Lee, Seoul (KR); Mi Jeoung Ahn, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/723,111

(22) Filed: Apr. 18, 2022

(65) Prior Publication Data

US 2022/0233170 A1 Jul. 28, 2022

Related U.S. Application Data

(63) Continuation of application No. 15/945,313, filed on Apr. 4, 2018, which is a continuation of application (Continued)

(30) Foreign Application Priority Data

Dec. 7, 2006 (KR) .......................... 10-2006-0123752

(51) Int. Cl.
*A61B 8/00* (2006.01)
*G06F 3/048* (2013.01)
(Continued)

(52) U.S. Cl.
CPC ................ *A61B 8/467* (2013.01); *A61B 8/00* (2013.01); *A61B 8/14* (2013.01); *A61B 8/4254* (2013.01);
(Continued)

(58) Field of Classification Search
CPC .. A61B 8/467; A61B 8/00; A61B 8/14; A61B 8/4254; A61B 8/4444; A61B 8/46;
(Continued)

(56) References Cited

U.S. PATENT DOCUMENTS 4,043,181 A 8/1977 Nigam
4,475,400 A 10/1984 Flax
(Continued)

FOREIGN PATENT DOCUMENTS

EP 0 539 697 A1 5/1993
EP 1 219 972 A2 7/2002
(Continued)

OTHER PUBLICATIONS

U.S. Office Action dated May 4, 2017 issued in U.S. Appl. No. 13/586,290.
(Continued)

*Primary Examiner* — Sanjay Cattungal
(74) *Attorney, Agent, or Firm* — Morgan, Lewis & Bockius LLP

(57) ABSTRACT

The present invention provides an ultrasound system, which comprises: a signal acquiring unit to transmit an ultrasound signal to an object and acquire an echo signal reflected from the object; a signal processing unit to control TGC (Time Gain Compensation) and LGC (Lateral Gain Compensation) of the echo signal; a TGC/LGC setup unit adapted to set TGC and LGC values based on TGC and LGC curves inputted by a user; and an image producing unit adapted to produce an ultrasound image of the object based on the echo signal. The signal processing unit is further adapted to control the TGC and the LGC of the echo signal based on the TGC and LGC values set by the TGC/LGC setup unit.

20 Claims, 8 Drawing Sheets

Related U.S. Application Data

No. 13/756,274, filed on Jan. 31, 2013, now Pat. No. 10,321,891, which is a continuation of application No. 13/184,094, filed on Jul. 15, 2011, now Pat. No. 8,403,855, which is a continuation of application No. 11/857,860, filed on Sep. 19, 2007, now Pat. No. 8,016,759.

(51) Int. Cl.
|  |  |
|---|---|
| *G06T 7/00* | (2017.01) |
| *G06F 3/04845* | (2022.01) |
| *G06F 3/01* | (2006.01) |
| *G06F 3/0484* | (2022.01) |
| *G06F 3/04847* | (2022.01) |
| *G01S 7/52* | (2006.01) |
| *A61B 8/14* | (2006.01) |
| *A61B 8/08* | (2006.01) |
| *A61B 6/00* | (2006.01) |

(52) U.S. Cl.
CPC .......... *A61B 8/4444* (2013.01); *A61B 8/46* (2013.01); *A61B 8/461* (2013.01); *A61B 8/462* (2013.01); *A61B 8/463* (2013.01); *A61B 8/465* (2013.01); *A61B 8/5207* (2013.01); *A61B 8/5269* (2013.01); *A61B 8/54* (2013.01); *G01S 7/52033* (2013.01); *G01S 7/52084* (2013.01); *G06F 3/01* (2013.01); *G06F 3/048* (2013.01); *G06F 3/0484* (2013.01); *G06F 3/04845* (2013.01); *G06F 3/04847* (2013.01); *G06T 7/0012* (2013.01); *A61B 6/467* (2013.01)

(58) Field of Classification Search
CPC ......... A61B 8/461; A61B 8/462; A61B 8/463; A61B 8/465; A61B 8/5207; A61B 8/5269; A61B 8/54; A61B 6/467; G01S 7/52033; G01S 7/52084; G06F 3/01; G06F 3/048; G06F 3/0484; G06F 3/04845; G06F 3/04847; G06T 7/0012
See application file for complete search history.

(56) References Cited

U.S. PATENT DOCUMENTS

| | | |
|---|---|---|
| 4,817,614 A | 4/1989 | Hassler et al. |
| 5,161,535 A | 11/1992 | Short et al. |
| 5,245,586 A | 9/1993 | Hassler |
| 5,257,624 A * | 11/1993 | Fraser ................. G01S 7/52033 |
| | | 600/437 |
| 5,315,999 A | 5/1994 | Kinicki et al. |
| 5,482,045 A | 1/1996 | Rust et al. |
| 6,063,030 A * | 5/2000 | Vara ....................... G16H 40/63 |
| | | 600/440 |
| 6,102,859 A | 8/2000 | Mo |
| 6,142,942 A | 11/2000 | Clark |
| 6,261,234 B1 * | 7/2001 | Lin ........................ A61B 8/445 |
| | | 600/463 |
| 6,368,279 B1 | 4/2002 | Liu |
| 6,468,212 B1 * | 10/2002 | Scott ..................... A61B 8/463 |
| | | 600/440 |
| 6,677,985 B1 | 1/2004 | Kubota et al. |
| 6,933,934 B2 | 8/2005 | Amemiya |
| 7,022,075 B2 | 4/2006 | Grunwald et al. |
| 8,016,759 B2 | 9/2011 | Lee et al. |
| 8,403,855 B2 | 3/2013 | Lee et al. |
| 9,072,471 B2 * | 7/2015 | Kato ...................... A61B 8/462 |
| 9,314,225 B2 * | 4/2016 | Steen .................... G01S 7/5208 |
| 10,456,111 B2 | 10/2019 | Lee |
| 10,517,572 B2 | 12/2019 | Kang |
| 11,020,091 B2 | 6/2021 | Jin |
| 2002/0008692 A1 | 1/2002 | Omura et al. |
| 2002/0087218 A1 | 7/2002 | Amemiya |
| 2003/0097071 A1 | 5/2003 | Halmann et al. |
| 2003/0187353 A1 | 10/2003 | Ng et al. |
| 2003/0195418 A1 * | 10/2003 | Barnes ................ G01S 7/52079 |
| | | 600/437 |
| 2003/0236459 A1 | 12/2003 | Loftman et al. |
| 2004/0015079 A1 | 1/2004 | Berger et al. |
| 2005/0059892 A1 | 3/2005 | Dubois et al. |
| 2005/0085730 A1 * | 4/2005 | Flesch ...................... A61B 8/12 |
| | | 600/459 |
| 2006/0020204 A1 * | 1/2006 | Serra ..................... G01S 7/5208 |
| | | 600/437 |
| 2007/0230759 A1 | 10/2007 | Tamura |
| 2007/0239019 A1 | 10/2007 | Richard et al. |
| 2009/0043195 A1 | 2/2009 | Poland |
| 2009/0069677 A1 | 3/2009 | Chen et al. |
| 2010/0049050 A1 | 2/2010 | Pelissier |
| 2010/0145195 A1 | 6/2010 | Hyun |
| 2010/0217128 A1 * | 8/2010 | Betts ..................... A61B 8/4254 |
| | | 345/184 |
| 2011/0043434 A1 | 2/2011 | Roncalez et al. |
| 2011/0054325 A1 | 3/2011 | Shin et al. |
| 2012/0133601 A1 * | 5/2012 | Marshall ................ G16H 40/63 |
| | | 345/173 |
| 2013/0030298 A1 | 1/2013 | Tamura |
| 2013/0064036 A1 | 3/2013 | Lee et al. |
| 2013/0144169 A1 | 6/2013 | Lee et al. |
| 2013/0226001 A1 * | 8/2013 | Steen .................... G01S 7/5208 |
| | | 600/447 |
| 2013/0239052 A1 * | 9/2013 | Moody .................... G06F 3/017 |
| | | 715/810 |
| 2013/0249842 A1 | 9/2013 | Vama |
| 2013/0324850 A1 * | 12/2013 | Petruzzelli ............. A61B 8/465 |
| | | 600/407 |
| 2014/0088428 A1 | 3/2014 | Yang et al. |
| 2014/0164965 A1 | 6/2014 | Lee et al. |
| 2014/0243669 A1 * | 8/2014 | Halmann ............. A61B 8/4427 |
| | | 600/443 |
| 2015/0121277 A1 | 4/2015 | Yoon |
| 2016/0007965 A1 | 1/2016 | Murphy |
| 2016/0120508 A1 | 5/2016 | Kim |
| 2016/0139789 A1 | 5/2016 | Jin et al. |

FOREIGN PATENT DOCUMENTS

| | | |
|---|---|---|
| JP | H06-154227 A | 6/1994 |
| JP | 10-248843 A | 9/1998 |
| JP | 2000-197637 A | 7/2000 |
| JP | 2006-296978 A | 11/2006 |
| KR | 10-2001-0067091 A | 7/2001 |
| KR | 10-2004-0069378 A | 8/2004 |
| KR | 2006-0033845 A | 4/2006 |

OTHER PUBLICATIONS

U.S. Office Action dated Oct. 8, 2013 issued in U.S. Appl. No. 13/938,847.
U.S. Final Office Action dated Mar. 13, 2014 issued in U.S. Appl. No. 13/475,686.
U.S. Office Action dated Mar. 21, 2014 issued in U.S. Appl. No. 13/938,847.
U.S. Office Action dated Mar. 26, 2015 issued in U.S. Appl. No. 13/475,686.
U.S. Non-Final Office Action dated Jul. 17, 2015 issued in U.S. Appl. No. 13/586,290.
U.S. Office Action dated Jun. 10, 2015 issued in U.S. Appl. No. 13/938,847.
U.S. Non-Final Office Action dated Jan. 5, 2016 issued in U.S. Appl. No. 14/866,038.
U.S. Office Action dated Mar. 3, 2016 issued in U.S. Appl. No. 13/586,290.
U.S. Office Action dated Jul. 1, 2016 issued in U.S. Appl. No. 14/866,038.
U.S. Office Action dated Aug. 2, 2013 issued in U.S. Appl. No. 13/475,686.

(56) References Cited

OTHER PUBLICATIONS

U.S. Office Action dated Nov. 22, 2022 issued in U.S. Appl. No. 15/945,313.

* cited by examiner

ULTRASOUND SYSTEM AND SIGNAL PROCESSING UNIT CONFIGURED FOR TIME GAIN AND LATERAL GAIN COMPENSATION

The present application is a Continuation Patent Application of U.S. patent application Ser. No. 15/945,313, filed on Apr. 4, 2018, which is a Continuation Patent Application of U.S. patent application Ser. No. 13/756,274, filed on Jan. 31, 2013, now U.S. Pat. No. 10,321,891, issued on Jun. 18, 2019, which is a Continuation Patent Application of U.S. patent application Ser. No. 13/184,094, filed on Jul. 15, 2011, now U.S. Pat. No. 8,403,855, issued on Mar. 26, 2013, which is a Continuation Patent Application of U.S. patent application Ser. No. 11/857,860, filed on Sep. 19, 2007, now U.S. Pat. No. 8,016,759, issued on Sep. 13, 2011, which claims priority from Korean Patent Application No. 10-2006-0123752 filed on Dec. 7, 2006, the entire subject matter of which is incorporated herein by reference.

BACKGROUND

1. Field

The present invention generally relates to an ultrasound system, and more particularly to an ultrasound system adapted to precisely and easily perform TGC (Time Gain Compensation) and LGC (Lateral Gain Compensation).

2. Background

An ultrasound system has become an important and popular diagnostic tool since it has a wide range of applications. Specifically, due to its non-invasive and non destructive nature, the ultrasound system has been extensively used in the medical profession. Modern high-performance ultrasound systems and techniques are commonly used to produce two or three-dimensional diagnostic images of internal features of an object.

In order to transmit and receive ultrasound signals, the ultrasound system is generally provided with a probe including a wideband transducer. When the transducer is electrically stimulated, it produces ultrasound signals and transmits them into a human body. The ultrasound signals transmitted into the human body are reflected from borders between human tissues and then returned to the transducer. The returned ultrasound echo signals are converted into electric signals. Thereafter, ultrasound image data for imaging the tissues is produced by amplifying and signal-processing the echo signals.

Typically, the ultrasound system is provided with a control panel including a plurality of input units in order to perform a control function of acquiring the ultrasound image, a menu control function, a measurement and annotation function, etc. The control panel is comprised of a touch panel, an image control unit, a measurement control unit, etc. The touch panel displays menus for optimizing an ultrasound image displayed on a display unit. The menus on the touch panel can be touched and selected by a user. The image control unit controls the ultrasound image, whereas the measurement control unit measures a distance to the object, a circumference of the object, etc. As illustrated in FIG. 1, the image control unit includes a plurality of TGC control keys 11 and a plurality of LGC control keys 12. The TGC control keys 11 are used to control a gain of each echo signal based on depth of the position from which the echo signal is reflected. Further, since the echo signal is attenuated at the outer right and left sides, the LGC control keys 12 are used to control a gain of the attenuated echo signal.

In the conventional system, the TGC control keys 11 and the LGC control keys 12 are arranged on different areas of the control panel. The problem associated with such an arrangement is that the size of the control panel must be inevitably increased. Further, a user of the system suffers a great inconvenience when operating the TGC control keys 11 and the LGC control keys 12. Another problem of the conventional system is that since the TGC control keys 11 and the LGC control keys 12 are comprised of slide-type variable resistors, it is very difficult for an unskilled user to finely control TGC and LGC with the TGC control keys 11 and the LGC control keys 12.

In order to resolve the above problems, the present invention is directed to providing an ultrasound system adapted to display a setup screen used to input TGC and LGC curves on a touch panel and perform TGC and LGC based on the inputted TGC and LGC curves.

The present invention provides an ultrasound system, which comprises: a signal acquiring unit adapted to transmit an ultrasound signal to an object and acquire an echo signal reflected from the object; a signal processing unit adapted to perform TGC (Time Gain Compensation) and LGC (Lateral Gain Compensation) upon the echo signal at a coarse compensation mode based on predetermined TGC and LGC values; an image producing unit adapted to produce an ultrasound image of the object based on the TGC and LGC compensated echo signal; an input unit adapted to allow a user to provide TGC and LGC curves; and a TGC/LGC setup processor adapted to set TGC and LGC values based on the TGC and LGC curves provided by the user. The signal processing unit is further adapted to perform the TGC and LGC upon the echo signal at a fine compensation mode based on the TGC and LGC values set by the TGC/LGC setup processor.

In addition, the present invention provides an ultrasound system, which comprises: a processor adapted to configure a setup screen for display; and a touch panel adapted to display the setup screen so as to allow a user to input TG and LGC curves. The processor is further adapted to calculate the TGC and LGC values based on the inputted TGC and the LGC curves.

BRIEF DESCRIPTION OF THE DRAWINGS

Arrangements and embodiments may be described in detail with reference to the following drawings in which like reference numerals refer to like elements and wherein.

DETAILED DESCRIPTION OF THE PRESENT INVENTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Certain embodiments of the present invention will be explained below with reference to FIGS. 2 to 8.

Figure 1:
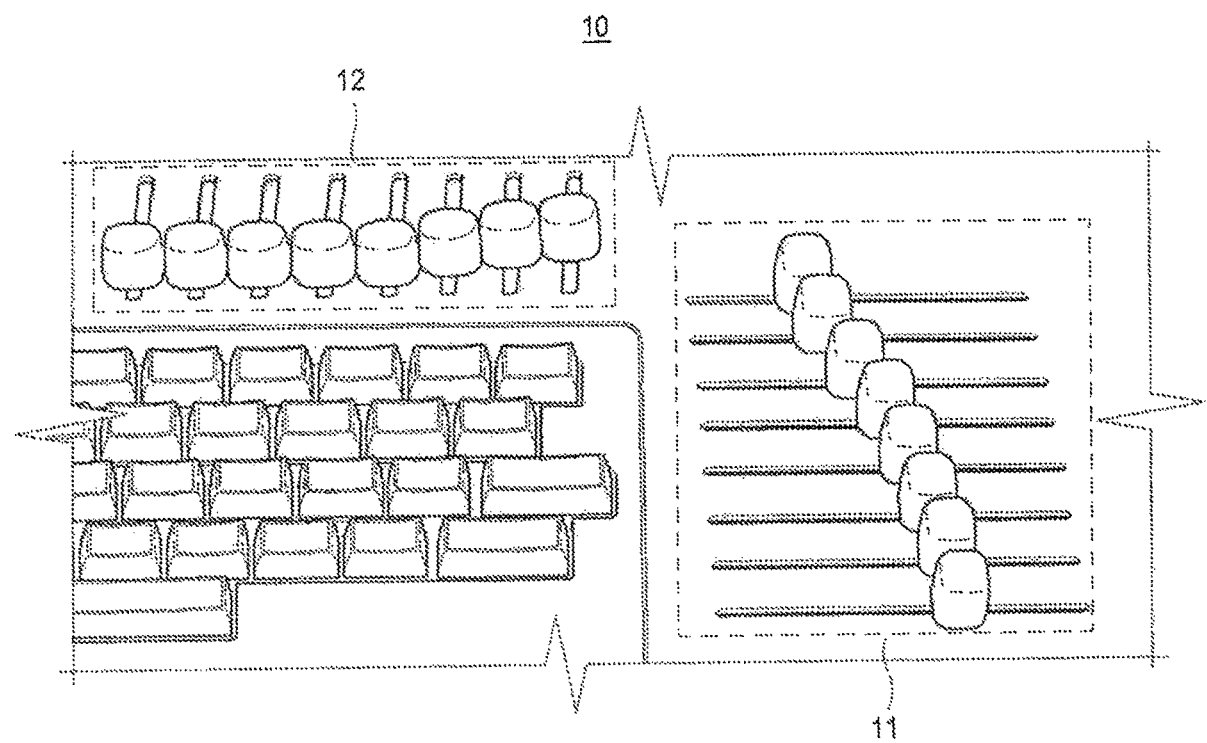
FIG. 1 is a schematic diagram illustrating conventional TGC and LGC control keys.
Figure 2:
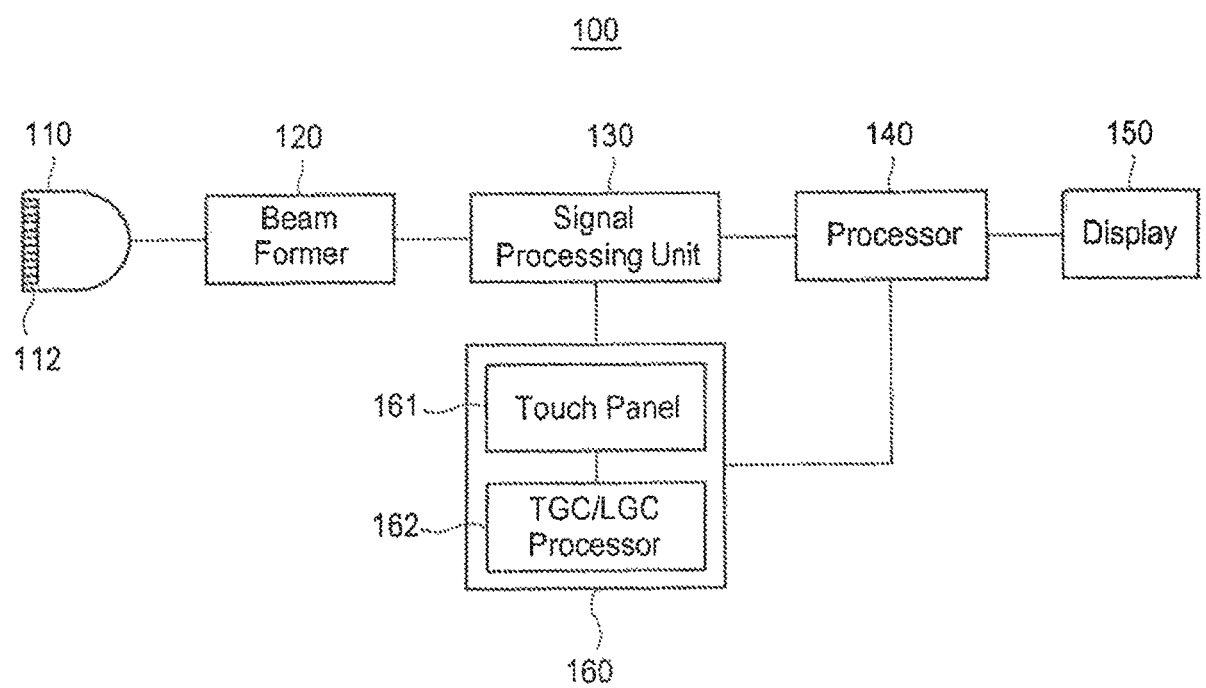
FIG. 2 is a block diagram showing a structure of an ultrasound system according to one embodiment of the present invention.
Figure 3:
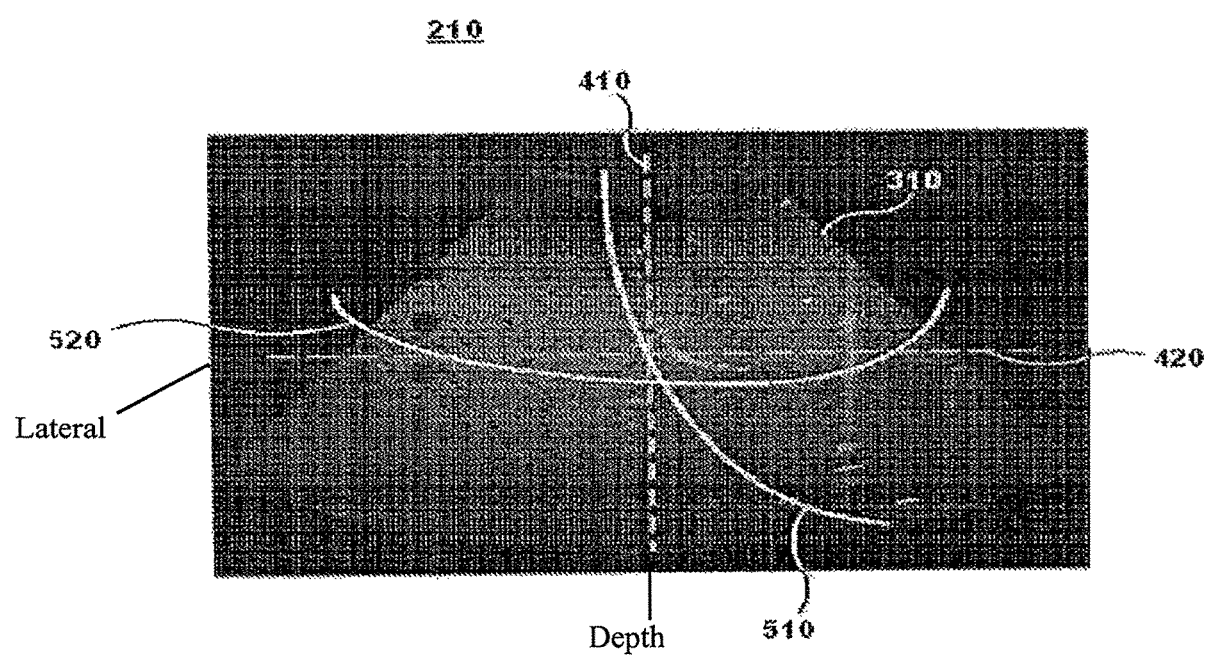
FIGS. 3 to 7 illustrate a setup screen according to one embodiment of the present.
Figure 4:
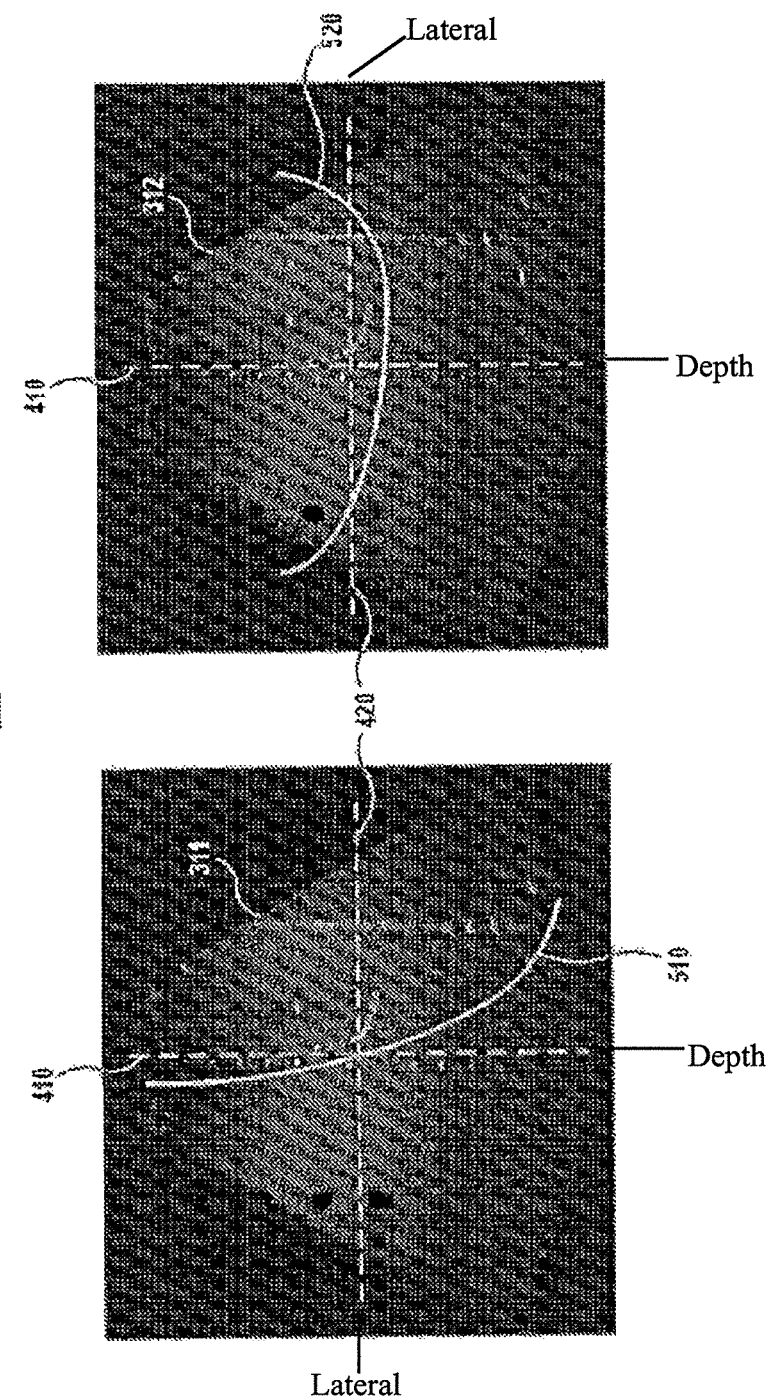
Figure 5:
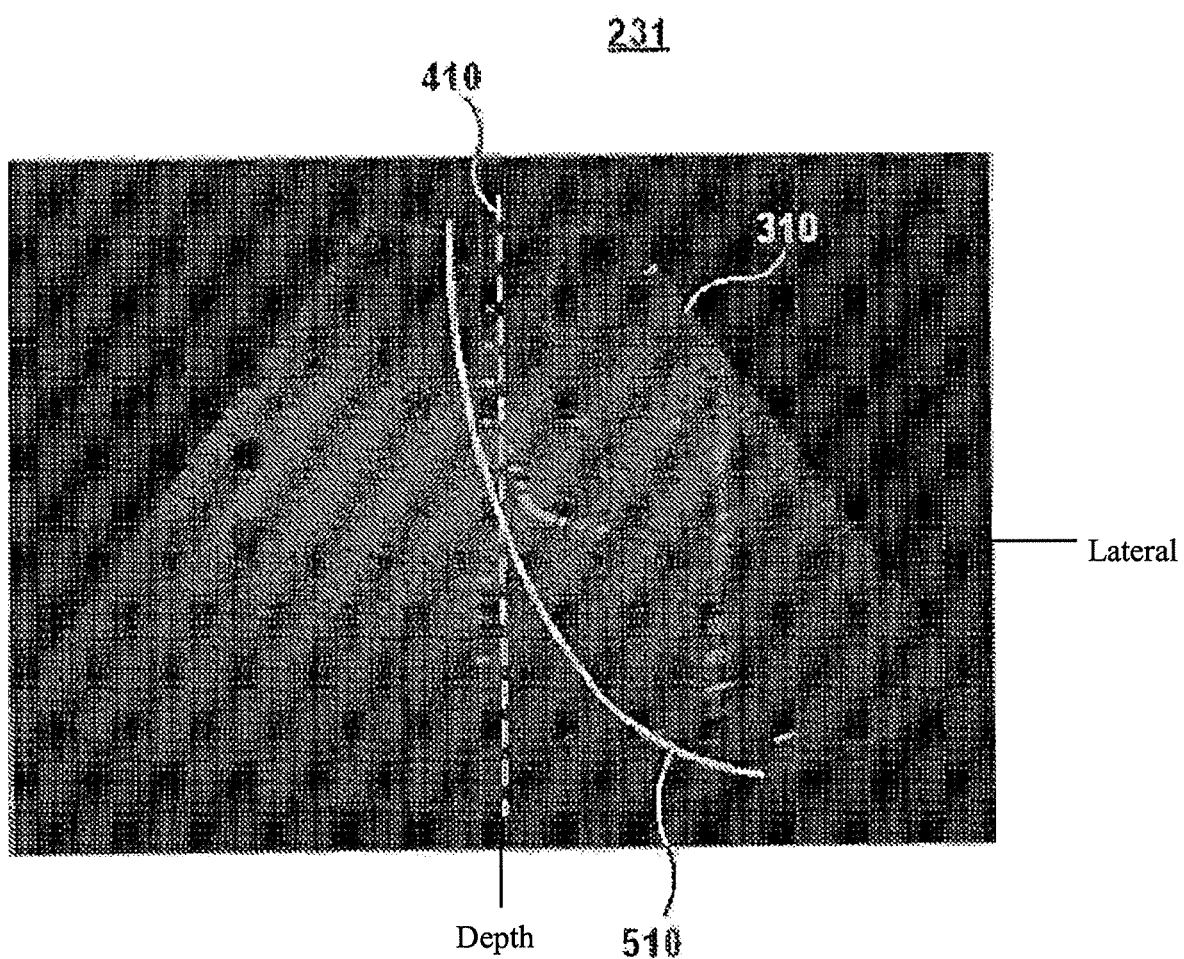
Figure 6:
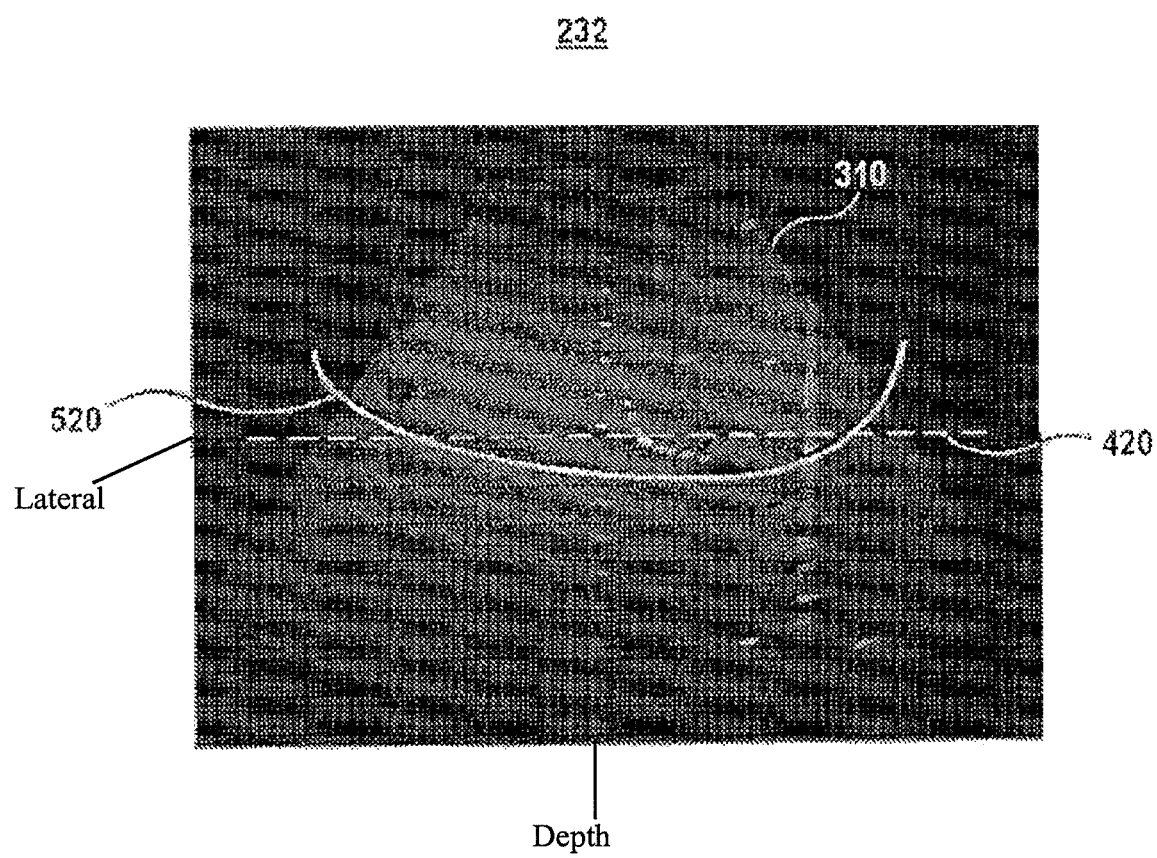
Figure 7:
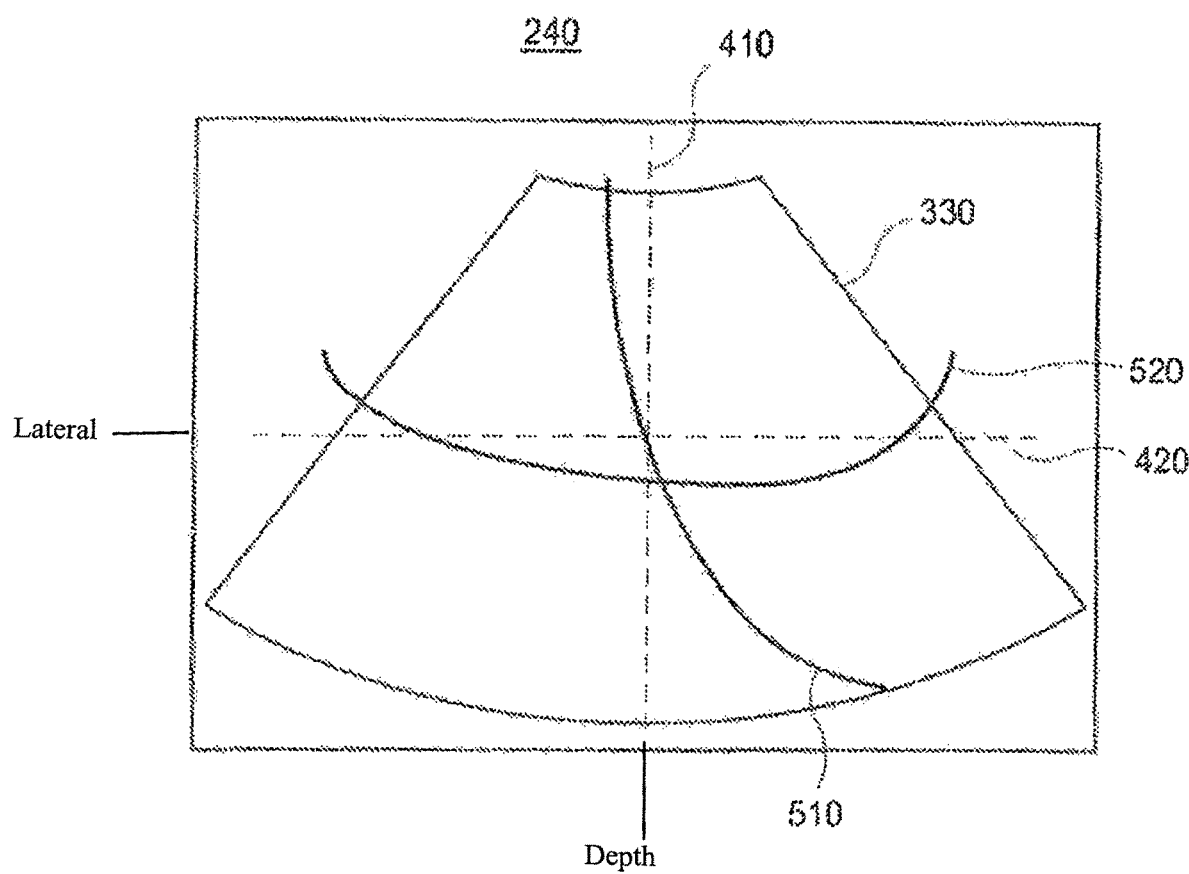

As illustrated in FIG. 2, an ultrasound system 100 comprises: a probe 110; a beam former 120; a signal processing unit 130; a processor 140; a display unit 150; and a TGC/LGC setup unit 160. The probe 110 includes a plurality of transducers 112. Each of the transducers 112 may be configured to transmit an ultrasound signal to an object and receive the ultrasound signal reflected from the object. The beam former 120 may be configured to focus the transmitted ultrasound signals from the transducers 112 on the object and collect the reflected ultrasound signals from the object to the transducers 112 together with corresponding time delay.

The signal processing unit 130 may be configured to amplify the signals collected by the beam former 120 and control gains of the amplified echo signals. Specifically, the signal processing unit 130 may be configured to perform TGC (Time Gain Compensation) and LGC (Lateral Gain Compensation) upon the echo signals based on predetermined TGC and LGC values at a coarse compensation mode (e.g., in an initial operation stage). The signal processing unit 130 may be further configured to perform TGC and LGC upon the echo signals based on TGC and LGC values calculated in a TGC/LGC setup unit 160 using a curve inputted by a user at a fine compensation mode (e.g., during operations).

The processor 140 may be configured to receive the echo signals from the signal processing unit 130 and produce an ultrasound image signal based on the echo signals. The display unit 150 may be adapted to receive the ultrasound image signal from the processor and display an ultrasound image based on the signal.

The TGC/LGC setup unit 160 may include a touch panel 161 and a TGC/LGC setup processor 162.

The touch panel 161 may be configured to display a setup screen and detect TGC/LGC curves inputted by the user on the touch panel 161 to produce a detecting signal. The touch panel 161 detects the user's input according to either the pressure sensing method or the electromagnetic induction method. The touch panel 161 may be a touch panel included in a control panel (not shown) of the ultrasound system 100. Alternatively, it may be separate and apart from the ultrasound system 100.

In one embodiment of the present invention, the touch panel 161 may be configured to display a setup screen 210 (shown in FIG. 3) including an ultrasound image 310 and first and second reference lines 410, 420. The ultrasound image 310 is based on the echo signal, the TGC and LGC of which are controlled based on the predetermined TGC and LGC values. The first and second reference lines 410, 420 may be used to detect a TGC curve 510 and a LGC curve 520 inputted by the user (i.e., to determine whether a curve inputted by the user is a TGC curve 510 or a LGC curve 520). After inputting a curve, the user can modify a portion of the curve.

In another embodiment of the present invention, the touch panel 161 may be configured to display a setup screen 220 (shown in FIG. 4) including first and second ultrasound images 311, 312 and first and second reference lines 410, 420. The first and second ultrasound images 311, 312 are based on the echo signal, the TGC and LGC of which are controlled based on the predetermined TGC and LGC values. The first and second reference lines 410, 420 may be used to detect whether a curve inputted by the user is a TGC curve 510 or a LGC curve 520. The first ultrasound image 311 may be identical to the second initial ultrasound image 312.

In yet another embodiment of the present invention, the touch panel 161 may be configured to display a first setup screen 231 (shown in FIG. 5) including an ultrasound image 310 and a first reference line 410. The ultrasound image 310 is based on the echo signal, the TGC and LGC of which are controlled based on the predetermined TGC and LGC values. The first reference line 410 may be used to detect a TGC curve 510 inputted by the user. The touch panel may then display a second setup screen 232 (shown in FIG. 6) including the ultrasound image 310 and a second reference line 420. The second reference lines 420 may be used to detect a LGC curve 520 inputted by the user. Alternatively, the touch panel 161 may be configured to display the second setup screen 232 before the first setup screen 231.

In still yet another embodiment of the present invention, the touch panel 161 may be configured to display a setup screen 240 (shown in FIG. 7) including a virtual ultrasound image 330 and first and second reference lines 410, 420.

The TGC/LGC setup processor 162 may be configured to detect TGC and LGC curves 510, 520 inputted by the user on the touch panel 161. The TGC/LGC setup processor 162 may then calculate new TGC and LGC values in consideration of the detected TGC and LGC curves and transmit the values to the signal processing unit 130.

Figure 8:
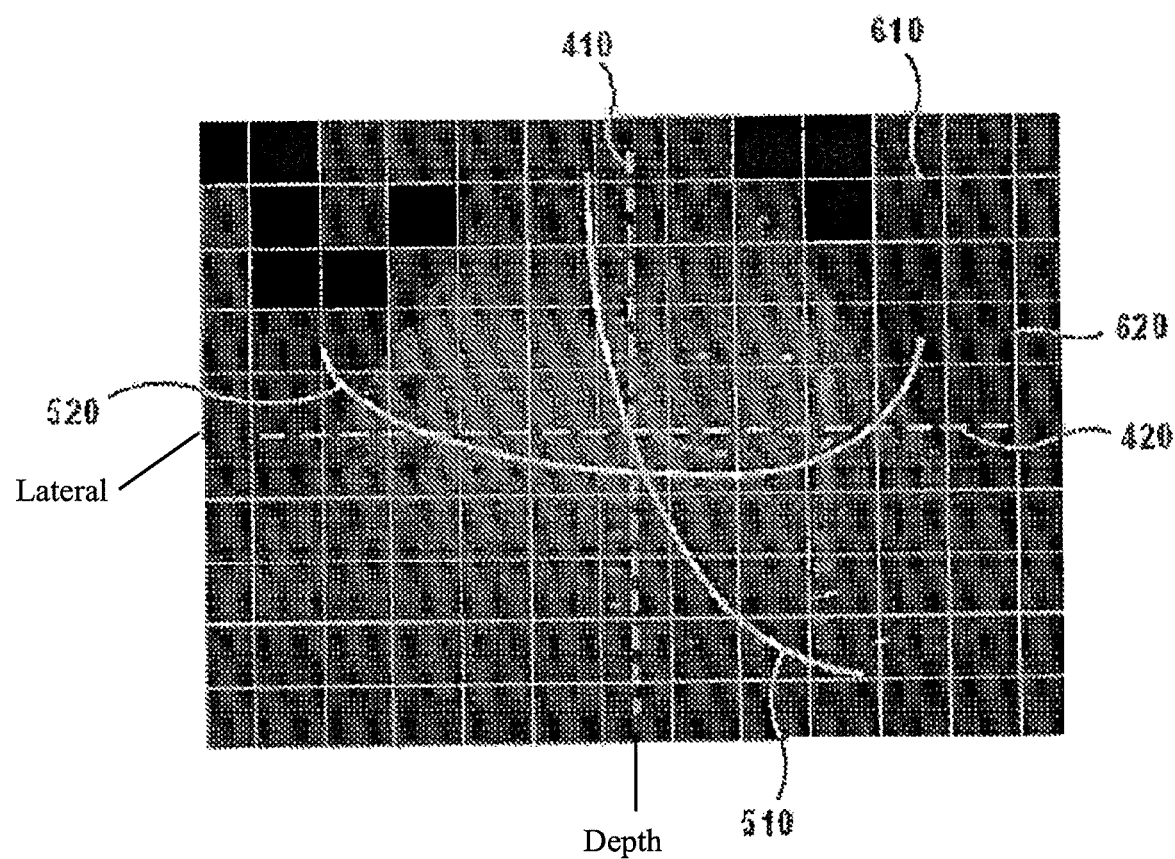
FIG. 8 illustrates an exemplary distinction between TGC and LGC curves according to one embodiment of the present invention.

In one embodiment of the present invention, as illustrated in FIG. 8, the TGC/LGC setup processor 162 may be configured to establish a first group of lines 610 and a second group of lines 620. The first group of lines 610 is perpendicular to a first reference line 410 and the lines in said group are equally spaced apart from each other. The second group of lines 620 is perpendicular to a second reference line 420 and the lines in this group are equally spaced apart from each other. If it is determined that a curve inputted by the user (such as the curve 510) intersects the first group of lines more often than the second group of lines, then the TGC/LGC setup processor 162 recognizes that the curve is a TGC curve. Alternatively, if it is determined that a curve inputted by the user (such as the curve 520) intersects the second group of lines more often than the first group of lines, then the TGC/LGC setup processor 162 recognizes that the curve is a LGC curve. The TGC/LGC setup processor 162 then calculates the new TGC value corresponding to the TGC curve 510 based on the first reference line 410. It also calculates the LGC value corresponding to the LGC curve 520 based on the second reference line 420. The TGC value and the LGC value are transmitted to the signal processing unit 130.

The present invention allows the user to accurately control the TGC and LGC by using the TGC and LGC curves inputted into the touch panel, thereby improving operational accuracy and time. Further, the present invention reduces the size of the control panel to thereby improve the spatial efficiency.

Although the present invention has been described with reference to a number of preferred embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   a probe configured for transmitting an ultrasound signal to an object and receiving echo signals reflected from the object;
   a touch panel; and
   a processor configured to receive, via the touch panel, a user's single curve touch input, the user's single curve touch input within a region where multiple vertical lines are visually displayed to intersect successively with two or more of multiple vertical lines, each of the multiple vertical lines corresponding to different lateral positions of an ultrasound image, and to adjust lateral gain compensation (LGC) values based on the successive intersection of the curve received by user's single curve touch input with the two or more of the multiple vertical lines,
   wherein the processor is configured to decide LGC values of two or more lateral positions of the ultrasound image corresponding to the two or more vertical lines of the multiple vertical lines, based on the successive intersection of the curve received by the user's single curve touch input with the two or more vertical lines.

2. The ultrasound system of claim 1, wherein the touch panel is further configured to display the multiple vertical lines.

3. The ultrasound system of claim 2, wherein the displayed multiple vertical lines are parallel with one another.

4. The ultrasound system of claim 1, wherein the ultrasound system further comprising a display configured to display the ultrasound image of the object,
   wherein the multiple vertical lines correspond to different lateral positions of the ultrasound image displayed on the display.

5. The ultrasound system of claim 1, wherein the touch panel is further configured to display the ultrasound image in a first area of the touch panel and the multiple vertical lines in a second area of the touch panel, the second area being different from the first area,
   wherein the multiple vertical lines displayed in the second area of the touch panel correspond to different lateral positions of the ultrasound image displayed in the first area of the touch panel.

6. The ultrasound system of claim 1, wherein the touch panel is further configured to display the intersection of the user's single curve touch input with the multiple vertical lines.

7. The ultrasound system of claim 1, wherein the touch panel is further configured to display a virtual image and to receive the user's single curve touch input over the displayed virtual image.

8. The ultrasound system of claim 7, wherein the virtual image comprises the multiple vertical lines.

9. The ultrasound system of claim 8, wherein two or more intersections of the user's single curve touch input with the multiple vertical lines are displayed on the virtual image.

10. The ultrasound system of claim 1, wherein the processor is further configured to control a gain of the echo signals from corresponding lateral positions based on the intersection of the user's single curve touch input with the multiple vertical lines corresponding to the different lateral positions.

11. An ultrasound system, comprising:
    a probe configured for transmitting an ultrasound signal to an object and receiving echo signals reflected from the object;
    a touch panel configured for receiving a single lateral gain compensation (LGC) curve touch input, the single LGC curve touch input within a region where multiple vertical lines are visually displayed to intersect successively with two or more of the multiple vertical lines, each of the multiple vertical lines corresponding to different lateral positions on the touch panel; and
    a processor configured for adjusting LGC setting for an ultrasound image of the object based on the successive intersection of the single LGC curve touch input with two or more of the multiple vertical lines.

12. The ultrasound system of claim 11, wherein the touch panel is further configured to display the multiple vertical lines.

13. The ultrasound system of claim 12, wherein the multiple vertical lines are vertically displayed and parallel with one another.

14. The ultrasound system of claim 11, wherein the multiple vertical lines correspond to different lateral positions of the ultrasound image of the object.

15. The ultrasound system of claim 11, wherein the ultrasound system further comprising a display configured to display the ultrasound image of the object,
    wherein the multiple vertical lines correspond to different lateral positions of the ultrasound image displayed on the display.

16. The ultrasound system of claim 11, wherein the touch panel is further configured to display the ultrasound image in a first area of the touch panel and to display the multiple vertical lines in a second area of the touch panel, the second area being different from the first area,
    wherein the multiple vertical lines displayed in the second area of the touch panel correspond to different lateral positions of the ultrasound image displayed in the first area of the touch panel.

17. The ultrasound system of claim 11, wherein the touch panel is further configured to display the successive intersection of the single LGC curve touch input with the multiple vertical lines.

18. The ultrasound system of claim 11, wherein the touch panel is further configured to display a virtual image and to receive the single LGC curve touch input over the displayed virtual image.

19. The ultrasound system of claim 18, wherein the virtual image comprises the multiple vertical lines.

20. The ultrasound system of claim 19, wherein two or more intersections of the single LGC curve touch input with the multiple vertical lines are displayed on the virtual image.

* * * * *